United States Patent
Inada et al.

(10) Patent No.: US 7,193,104 B2
(45) Date of Patent: Mar. 20, 2007

(54) BIS-β-HYDROXYETHYL TEREPHTHALATE PRODUCTION PROCESS AND PURIFICATION PROCESS

(75) Inventors: Shuji Inada, Suita (JP); Kikuchi Sato, Fukuyama (JP)

(73) Assignee: Aies Co., Ltd. (JP)

( * ) Notice: Subject to any disclaimer, the term of this patent is extended or adjusted under 35 U.S.C. 154(b) by 437 days.

(21) Appl. No.: 10/623,002

(22) Filed: Jul. 18, 2003

(65) Prior Publication Data

US 2004/0019234 A1   Jan. 29, 2004

Related U.S. Application Data

(62) Division of application No. 09/622,518, filed as application No. PCT/JP99/07284 on Dec. 24, 1999, now Pat. No. 6,630,601.

(30) Foreign Application Priority Data

| Aug. 4, 1999 | (JP) | ............... 11-220804 |
| Aug. 5, 1999 | (JP) | ............... 11-222663 |
| Aug. 5, 1999 | (JP) | ............... 11-222664 |
| Aug. 10, 1999 | (JP) | ............... 11-226033 |

(51) Int. Cl.
   *C07C 69/76*   (2006.01)
(52) U.S. Cl. ...................................................... 560/76
(58) Field of Classification Search ................. 560/76, 560/78, 79, 103
   See application file for complete search history.

(56) References Cited

FOREIGN PATENT DOCUMENTS

IN           145323      *  9/1978
JP          06166747     *  6/1994

OTHER PUBLICATIONS

Patent Abstracts of Japan Publication No. 06-166747, published on Jun. 14, 1994 in the name of assignee Toray Ind. Inc. by inventors Morita Toru and Okasaka Hidesada entitled Depolymerization of Aromatic Polyester.

* cited by examiner

Primary Examiner—Joseph K. McKane
Assistant Examiner—Karl Puttlitz
(74) Attorney, Agent, or Firm—Anderson Kill & Olick, PC

(57) ABSTRACT

An aromatic polyester is pre-decomposed by heating together with bis-β-hydroxyethyl terephthalate and/or a low condensate thereof and then, reacted with ethylene glycol to convert the terephthalic acid component of the pre-decomposed product into bis-β-hydroxyethyl terephthalate and/or a low condensate thereof.

The thus obtained solution composition, that is, bis-β-hydroxyethyl terephthalate solution composition containing ethylene glycol, bis-β-hydroxyethyl terephthalate and cations and/or anions as impurities is brought into contact with a cation exchanger and/or an anion exchanger to remove cations and anions as impurities to produce bis-β-hydroxyethyl terephthalate having a small content of ions.

The bis-β-hydroxyethyl terephthalate-containing mixture having a small content of ions is subjected to preliminary evaporation or distillation to distill off a compound having a boiling point lower than that of bis-β-hydroxyethyl terephthalate and then, to evaporation or distillation under reduced pressure to give purified bis-β-hydroxyethyl terephthalate.

Thus, purified bis-β-hydroxyethyl terephthalate having a cation and anion total content of 15 ppm or less is obtained.

6 Claims, No Drawings

BIS-β-HYDROXYETHYL TEREPHTHALATE PRODUCTION PROCESS AND PURIFICATION PROCESS

This application is a divisional of U.S. Ser. No. 09/622,518 filed on Aug. 17, 2000 now U.S. Pat. No. 6,630,601, which is a 371 of PCT/JP99/07284 filed Dec. 24, 1999

TECHNICAL FIELD

The present invention relates to a process for producing bis-β-hydroxyethyl terephthalate and/or a low condensate thereof from an aromatic polyester and to a process for purifying bis-β-hydroxyethyl terephthalate or a low condensate thereof. More specifically, it relates to a process capable of producing bis-β-hydroxyethyl terephthalate and/or a low condensate thereof efficiently even from an recovered aromatic polyester and to a process capable of purifying bis-β-hydroxyethyl terephthalate and/or a low condensate thereof obtained by the above process, to a high level.

PRIOR ART IN THE TECHNICAL FIELD

One of the characteristic features of aromatic polyesters is that they have excellent performance suitable for use in the field of a wide variety of molded products such as fibers, films or resins. Another characteristic feature of the aromatic polyesters is that it is relatively easy to return them to a raw material stage by depolymerization.

Aromatic polyesters, especially terephthalate-based polyesters centering on polyethylene terephthalate are widely used in the field of various molded products as described above. As means of producing an aromatic polyester, there is currently used a process comprising the steps of forming an intermediate containing bis-β-hydroxyethyl terephthalate by a direct esterification reaction between terephthalic acid and ethylene glycol or an ester exchange reaction between a lower alkyl ester of terephthalic acid, especially dimethyl terephthalate, and ethylene glycol and then, generally subjecting the intermediate directly to the polycondensation step at a high temperature under high vacuum. The aromatic polyester can be returned to a raw material stage by depolymerization and polycondensed again to produce a polyester. Therefore, it can be said that it is an excellent material from the viewpoint of resource saving because it can be recycled.

To depolymerize a terephthalate-based polyester, a depolymerization reaction has been heretofore generally carried out basically in a reaction system containing the polyester and an excess of ethylene glycol as the main constituent components. In order to carry out the reaction smoothly, it is important to create a state where the polyester is easily depolymerized. When an amorphous polyester is used as a raw material, the depolymerization reaction proceeds relatively easily. However, when the polyester is in the form of a fiber having high crystallinity, the depolymerization reaction relatively hardly proceeds in most cases. When the polyester is in the form of a bottle which is a resin molded product, there is a tendency that depolymerization hardly proceeds in a neck portion where crystallization is in progress, of the bottle.

On the other hand, the purification of crude bis-β-hydroxyethyl terephthalate, obtained by depolymerization, to a high level is very important when a high-quality aromatic polyester is to be produced using the bis-β-hydroxyethyl terephthalate again as a raw material.

A typical method for the purification of the crude bis-β-hydroxyethyl terephthalate is a purification method by recrystallization. Although bis-β-hydroxyethyl terephthalate obtained by this method appears to have high quality, impurities still remain practically and become obstacles to the acquisition of a high-quality polyester in most cases. Particularly when a polyester is to be recovered and depolymerized into bis-β-hydroxyethyl terephthalate to obtain a polyester again, the above obstacles are markedly observed in most cases.

Meanwhile, JP-A48-86841 (the term "JP-A" as used herein means an "unexamined published Japanese patent application") discloses a process for purifying bis-β-hydroxyethyl terephthalate or a mixture of bis-β-hydroxyethyl terephthalate and terephthalic acid by treating it with water and then separating water, wherein the separated water is treated with an ion exchange resin and absorbent, and recycled for re-use.

In the above purification process, bis-β-hydroxyethyl terephthalate is treated with water for purification and an ion exchange resin or absorbent is not used directly for the purification of bis-β-hydroxyethyl terephthalate.

DISCLOSURE OF THE INVENTION

It is an object of the present invention to provide a process for producing bis-β-hydroxyethyl terephthalate and/or a low condensate thereof from an aromatic polyester.

It is another object of the present invention to provide a process for producing bis-β-hydroxyethyl terephthalate and/or a low condensate thereof, which can efficiently decompose a highly crystallized aromatic polyester, for example, even a recovered aromatic polyester fiber, fiber layer or film, or a recovered bottle having a highly crystallized neck portion.

It is still another object of the present invention to provide a process for producing high-purity bis-β-hydroxyethyl terephthalate.

It is a further object of the present invention to provide a process for producing high-purity bis-β-hydroxyethyl terephthalate by removing, as much as possible, ions which are impurities contained therein inevitably, for example, ions derived from an esterification catalyst or an ester exchange catalyst.

It is a still further object of the present invention to provide a process for producing high-purity bis-β-hydroxyethyl terephthalate from bis-β-hydroxyethyl terephthalate obtained by glycol-decomposition of a recovered polyethylene terephthalate.

It is a still further object of the present invention to provide highly purified bis-β-hydroxyethyl terephthalate having an extremely small content of cations and/or anions.

Other objects and advantages of the present invention will become apparent from the following description.

According to the present invention, firstly, the above objects and advantages of the present invention are attained by a process for producing bis-β-hydroxyethyl terephthalate and/or a low condensate thereof from an aromatic polyester (may be referred to as "first process of the present invention" hereinafter), comprising the steps of:

heating an aromatic polyester comprising terephthalic acid as a main dicarboxylic acid component and ethylene glycol as a main glycol component together with bis-β-hydroxyethyl terephthalate and/or a low condensate thereof to pre-decompose the aromatic polyester; and then, reacting the obtained pre-decomposed product with ethylene glycol to convert the terephthalic acid component of the pre-decomposed product into bis-β-hydroxyethyl terephthalate and/or a low condensate thereof.

According to the present invention, secondly, the above objects and advantages of the present invention are attained by a process for producing bis-β-hydroxyethyl terephthalate having a small content of ions (may be referred to as "second process of the present invention" hereinafter), comprising the step of:

bringing a bis-β-hydroxyethyl terephthalate solution composition comprising ethylene glycol, bis-β-hydroxyethyl terephthalate and cations and/or anions as impurities into contact with a cation exchanger and/or an anion exchanger to reduce the total content of cations and anions as impurities to 50 ppm or less based on the bis-β-hydroxyethyl terephthalate.

According to the present invention, thirdly, the above objects and advantages of the present invention are attained by a process for purifying bis-β-hydroxyethyl terephthalate (may be referred to as "third process of the present invention" hereinafter), comprising the steps of:

(1) obtaining a crude bis-β-hydroxyethyl terephthalate by subjecting a bis-β-hydroxyethyl terephthalate-containing mixture containing cations and anions in a total amount of 50 ppm or less, ethylene glycol in an amount of more than 10 wt % and a compound having a boiling point lower than that of bis-β-hydroxyethyl terephthalate to preliminary evaporation or distillation to distill off the compound having a boiling point lower than that of bis-β-hydroxyethyl terephthalate; and then, (2) subjecting the crude bis-β-hydroxyethyl terephthalate to evaporation or distillation under reduced pressure to separate purified bis-β-hydroxyethyl terephthalate.

Further, according to the present invention, fourthly, the above objects and advantages of the present invention are attained by a process for purifying bis-β-hydroxyethyl terephthalate (may be referred to as "fourth process of the present invention" hereinafter) comprising the step of:

subjecting crude bis-β-hydroxyethyl terephthalate having a cation and anion total content of 50 ppm or less to evaporation or distillation under reduced pressure.

Finally, according to the present invention, the above objects and advantages of the present invention are attained by purified bis-β-hydroxyethyl terephthalate containing cations and anions in a total content of 15 ppm or less.

PREFERABLE EMBODIMENT OF INVENTION

Heretofore, for the depolymerization of a terephthalate-based polyester, the polyester has been supplied in at least one of such forms as a pellet, film, flake, thread and mass into a reaction system. In the reaction system, the polyester which can take the above forms is made fine gradually and finally loses its form. The time required for coming to this stage varies according to the type, form and crystallinity of the polyester to be supplied, the degree of orientation, reaction conditions such as temperature, the quality of agitation and the type of a reactor. Although desired reaction conditions can be set by studying optimization in advance, the type, form and crystal state of a terephthalate-based polyester to be supplied into the system differ every time it is acquired in most cases, which greatly influences the proceeding of a reaction and interferes with actual operation frequently. The first process of the present invention is a process for carrying out a depolymerization reaction smoothly. A description will be first given of the first process of the present invention.

In the first process of the present invention, the aromatic polyester comprises terephthalic acid as a main acid component and ethylene glycol as a main glycol component and encompasses an aromatic polyester which further comprises a small amount of at least one other component as a copolymer component. The amount of the comonomer component is generally 40 mol % or less, preferably 30 mol % or less, more preferably 20 mol % or less based on the total of all the constituent units. Examples of the copolymer component include, as the dicarboxylic acids, aromatic dicarboxylic acids such as isophthalic acid, diphenyldicarboxylic acid, diphenylsulfonedicarboxylic acid, diphenylether dicarboxylic acid, naphthalenedicarboxylic acid, diphenoxyethanedicarboxylic acid and sodium sulfoisophthalic acid; aliphatic dicarboxylic acids such as sebacic acid and adipic acid; and alicyclic dicarboxylic acids such as hexahydroterephthalic acid; and as the diols, trimethylene glycol, tetramethylene glycol, hexamethylene glycol, cyclohexane dimethanol, bis-β-hydroxyethyl bisphenol A, bis-β-hydroxyethoxy diphenylsulfone, bis-β-hydroxyethoxydiphenyl ether, diethylene glycol, polyethylene glycol and the like. Hydroxycarboxylic acids such as p-hydroxyethoxybenzoic acid may also be used. Further, a polyfunctional compound having 3 or more functional groups and/or a monofunctional compound may be used in conbination in limits that the polyester is maintained in the linear form. Illustrative examples of the polyfunctional compound having 3 or more functional groups include trimesic acid, glycerin, pentaerythritol and the like, and illustrative examples of the monofunctional compound include diphenylmonocarboxylic acid, diphenylether monocarboxylic acid, phenoxypolyethylene glycol and the like. These comonomers may be used alone or in combination of two or more as a functional derivative such as an ester.

In the first process of the present invention, the aromatic polyester is first heated together with bis-β-hydroxyethyl terephthalate and/or a low condensate thereof to pre-decompose the aromatic polyester. The term "low condensate" as used herein denotes a compound containing ethylene terephthalate as the main constituent component of a recurring unit and having a low degree of polymerization, generally in the form of a mixture. The average polymerization degree of the low condensate is 1 to about 10, preferably 1 to about 6, more preferably 1 to about 3. The heating temperature is preferably a temperature at which bis-β-hydroxyethyl terephthalate and/or a low condensate thereof in the reaction system melt/melts. Specifically, it is 150 to 265° C., more preferably 200 to 245° C. As for the quantitative relationship between the aromatic polyester and bis-β-hydroxyethyl terephthalate and/or a low condensate thereof in pre-decomposition which can be changed as required, the bis-β-hydroxyethyl terephthalate and/or low condensate thereof is generally preferably used in an amount of 0.1 to 4.5 parts by weight, particularly preferably 0.7 to 1.2 parts by weight based on 1 part by weight of the aromatic polyester. The pre-decomposition reaction time generally varies according to the quantitative relationship between the aromatic polyester and bis-β-hydroxyethyl terephthalate and/or low condensate thereof, the type, form and crystallinity of the polyester to be supplied, the degree of orientation, reaction conditions such as temperature, the quality of agitation and the type of a reactor as described above. Although it cannot be specified unconditionally, it is preferably 0.5 to 5.0 hours, particularly preferably 0.5 to 1.5 hours. The pre-decomposition reaction may be carried out at normal pressure or increased pressure. It may also be carried out under reduced pressure at which a distillate from the reaction system does not impede the proceeding of the reaction. Although it is desired that free ethylene glycol should not be contained in the bis-β-hydroxyethyl terephthalate and/or low condensate thereof used in the pre-decomposition reaction, the existence of a small amount of ethylene glycol is permitted. In this case, the amount of ethylene glycol which is existent in a small amount should not impede the above pre-decomposition reaction. Ethylene glycol may one that has remained as a result of the reaction, may be newly added or in an admixture of both. The permissible amount of ethylene glycol is preferably about 1.0 part or less by weight, more preferably 0.5 part or less by weight based on 1 part by weight of the bis-β-hydroxyethyl terephthalate and/or low condensate thereof. As for the pre-decomposition reaction, the aromatic polyester and bis-β-hydroxyethyl terephthalate and/or low condensate thereof may be reacted with each other at one time, or one or both of them may be divided into two parts or more, introduced into the system to react with each other. Further, it is possible and preferred that the product of a reaction for obtaining bis-β-hydroxyethyl terephthalate and/or a low condensate thereof by reacting the pre-decomposition product with ethylene glycol, that is carried out subsequently to the pre-decomposition reaction, should be used as at least part of the bis-β-hydroxyethyl terephthalate and/or low condensate thereof to be used in the pre-decomposition reaction. In this case, the existence of a small amount of ethylene glycol is permitted as described above.

In the first process of the present invention, a reaction for decomposing the pre-decomposition product into bis-β-hydroxyethyl terephthalate and/or a low condensate thereof by reacting the pre-decomposition product with ethylene glycol, that is, a reaction for converting the terephthalic acid component of the pre-decomposition product into bis-β-hydroxyethyl terephthalate and/or a low condensate thereof is carried out subsequently to the pre-decomposition.

This reaction is preferably carried out at a temperature of 190 to 265° C., more preferably 200 to 220° C. Good results are obtained when ethylene glycol is used in an amount of 0.3 to 10.0 parts by weight, preferably 3.0 to 5.0 parts by weight based on 1 part by weight of the pre-decomposition product. The reaction may be carried out in the above ratio from the beginning of the reaction, or one or both of the reactants may be divided into two parts or more. Since the reaction time varies according to reaction conditions such as temperature, the quality of agitation, the form of a reactor and the like and division of the addition is possible as described above, it cannot be specified unconditionally. However, it is preferably 1.0 to 8.0 hours, more preferably 1.5 to 2.5 hours. The reaction may be carried out at normal pressure or increased pressure. It may be carried out under reduced pressure at which a distillate from the reaction system does not impede the proceeding of the reaction.

It is recommended to add an appropriate reaction catalyst in order to carry out the reaction smoothly. Illustrative examples of the reaction catalyst include known ester exchange reaction catalysts such as sodium and magnesium methylates, fatty acid salts and carbonates of Zn, Cd, Mn, Co, Ca and Ba such as zinc borate and zinc acetate, metal Na and Mg, and oxides thereof. They may be used alone or in combination of two or more. The amount of the reaction catalyst is generally about 0.05 to 3.0 wt % based on the raw material terephthalate-based polyester.

The above reactions in the first process of the present invention may be carried out in a so-called batch method that the raw materials are supplied into a reactor in the above-described amount ratios and reacted and then, the reaction product is taken out after the end of the reaction or in, a so-called continuous method that the supply of the raw materials and take-out are carried out continuously. Or, it may be carried out in a combination of the two methods.

According to the results of studies conducted by the inventors of the present invention, a polyester obtained by using the bis-β-hydroxyethyl terephthalate and/or low condensate thereof obtained by the first process of the present invention as at least one of its raw materials may be used in various molded products such as fibers, films and bottles. Further, when a polyester molded products is to be depolymerized and substantially returned to the stage of bis-β-hydroxyethyl terephthalate, the obtained depolymerized product can be obtained as a solution containing ethylene glycol as a main solvent by carrying out a depolymerization step using ethylene glycol as described above. High-quality bis-β-hydroxyethyl terephthalate can be obtained by subjecting the above solution, directly or after adjustment of its concentration to an appropriate level, to a catalyst removing step as required and a cation and anion removing step as will be detailed hereinafter. In this case, substantially colorless high-quality bis-β-hydroxyethyl terephthalate can be easily obtained by carrying out at least one time of a decoloring step as required before, during or after the above step.

The bis-β-hydroxyethyl terephthalate obtained by carrying out the first process of the present invention can be used as at least one of raw materials for the re-production of a high-quality polyester in the form of a solution as it is or in a state of a solution whose concentration has been adjusted to an appropriate level or upon being subjected to a recrystallization step or distillation step. In this case, even when a polyester molded product to be depolymerized is in a state of a mixture of it and other material or a mixture of it and foreign matter such as dust as in the case of a commodity, the present invention can be carried out smoothly by employing a foreign matter removing step such as selection or filtration as required. For example, when a polyester is in the form of a fibrous commodity, it is mixed with a different kind of fiber or contains an inorganic substance such as titanium oxide, when a polyester is in the form of a film, it is mixed with various film materials such as polyethylene or polyamide or contains a lubricant, and when a polyester is in the form of other molded product such as a bottle, it is crushed and mixed with such a material as polyethylene or the like used in a cover portion or bottom portion, or mixed with various materials such as paper and plastic for use in a label, all of which are very common. According to the results of studies conducted by the present inventors, it is possible to attain an intended object by carrying out a conventionally known method such as liquid-liquid separation or solid-liquid separation and using the process of the present invention and the above-described methods as required.

A description will be subsequently given of the second process of the present invention.

The starting material used in the present invention is a bis-β-hydroxyethyl terephthalate solution composition comprising ethylene glycol, bis-β-hydroxyethyl terephthalate and cations and/or anions as impurities.

This solution composition may be prepared by any method. For example, it may be a reaction product produced by a direct esterification reaction between ethylene glycol and terephthalic acid or an ester exchange reaction between ethylene glycol and dimethyl terephthalate. Further, it may be a decomposition product produced by decomposing a recovered polyethylene terephthalate or waste polyethylene terephthalate which is not accepted as a commercial product with ethylene glycol, or a decomposition product obtained by the first process of the present invention. Alternatively, it may be a mixture derived from the above products.

For example, a solution composition comprising, as a main solute, bis-β-hydroxyethyl terephthalate produced from unpurified terephthalic acid as a raw material can be highly purified by the process of the present invention.

The reaction product and the decomposition product generally contain an esterification catalyst, ester exchange catalyst or polycondensation catalyst.

The cations and anions as impurities in the present invention are generally derived from these catalysts. The decomposition product of the recovered polyethylene terephthalate or waste polyethylene terephthalate may contain cations and anions as impurities derived from additives added to polyethylene terephthalate for other purposes such as antistatic purpose, various kinds of unexpected dirt or the like. The present invention is effective in removing these impurities.

The above solution composition used as the starting material in the present invention comprises ethylene glycol and bis-β-hydroxyethyl terephthalate as main components and anions and cations as impurities generally in an amount of 3,000 ppm or less based on the bis-β-hydroxyethyl terephthalate. Of the above amount, the cations are generally contained in an amount of 2,500 ppm or less and the anions in an amount of 500 ppm or less based on the same basis.

The above solution composition may contain a glycol other than ethylene glycol or a bis-ester form other than bis-β-hydroxyethyl terephthalate.

This is understood from the fact that the solution composition of the present invention includes a depolymerized product of a copolymer which is essentially composed of ethylene terephthalate as the recovered or waste terephthalate-based polyester and contains, as a copolymer component, a subordinate constituent component in small quantities. Illustrative examples of the terephthalate-based polyester are the same as those listed for the first process of the present invention.

It is understood that when the above solution composition in the second process of the present invention contains comonomer components derived from a terephthalate-based polyester, the comonomer components are a bis-ester form other than bis-β-hydroxyethyl terephthalate as a dicarboxylic acid component and a glycol other than ethylene glycol as a diol component.

The solution composition in the second process of the present invention preferably contains bis-β-hydroxyethyl terephthalate in an amount of 5 to 80 wt %, more preferably 8 to 40 wt %, particularly preferably 10 to 30 wt %, based on the solution composition. The above solution composition preferably comprises ethylene glycol as a main solvent and bis-β-hydroxyethyl terephthalate as a main solute.

The above solution composition is brought into contact with a cation exchanger and/or an anion exchanger in the second process of the present invention.

The cation exchanger and the anion exchanger may be particulate, chain-like, fibrous or amorphous. For example, when the ion exchanger is particulate, it is charged into a column and the solution composition is let pass through the charged column to bring the composition into contact with the ion exchanger.

The cation exchanger is preferably a cation exchange resin and the anion exchanger is preferably an anion exchange resin.

The cation exchange resin is preferably a cation exchange resin having —SO$_3$H, —COOH, —N(CH$_2$COOH)$_2$ or the like as a cation exchange functional group. The cation exchange resin products available on the market include SK series, PK series, WK series of Dia Ion (Mitsubishi Chemical Corporation), and IR series and IRC series of Amberlite (Rohm and Haas Japan Co., Ltd.). These commodities are generally converted into cation exchange resins having the above free acid groups when in use because their ion exchange functional groups are stabilized as a sodium salt and the like.

The anion exchange resin is an anion exchange resin having, for example,

as an anion exchange functional group. The anion exchange resin products available on the market include SA series, PA series and WA series of Dia Ion (Mitsubishi Chemical Corporation) and IRA series and IRA-900 series of Amberlite (Rohm and Haas Japan Co., Ltd.). These commodities are generally converted into anion exchange resins having the above hydroxyl group anions when in use because their ion exchange functional groups are stabilized as groups having halogen anions and not hydroxyl ions (OH$^-$).

The anion exchange resins in a gel type are divided into a crack type and a non-crack type. The non-cracking type is preferred because the amount of bis-β-hydroxyethyl terephthalate adsorbed is smaller than that of the cracking type.

Further, a so-called MR type (microporous type) ion exchange resin which is more excellent in physical durability and has higher exchange adsorption rate than a gel type may also be used.

Either one of the cation exchanger and anion exchanger or both may be used. When absolution composition containing cations and anions as impurities contains one of them in an extremely large amount and the other in a negligible amount, only an ion exchanger for removing the former one can be used.

Generally speaking, both a cation exchanger and an anion exchanger are preferably used. In this case, the solution composition may be brought into contact with the cation exchanger and the anion exchanger at the same time or sequentially. For example, when the solution composition is brought into contact with a mixture of the cation exchange resin and the anion exchange resin, it is contacted to both of them at the same time and when it is contacted with a column filled with the cation exchange resin and to a column filled with the anion exchange resin sequentially, it is contacted with both of them sequentially. Preferably, the solution composition is first brought into contact with the cation exchanger and then with the anion exchanger sequentially.

The contact of the solution composition with the cation exchanger and the anion exchanger must be carried out at a temperature at which the crystals of bis-β-hydroxyethyl terephthalate do not separate out from the solvent and which is lower than the maximum use temperature of the ion exchange resins, preferably 20 to 120° C., more preferably 30 to 70° C.

The contact may be carried out at normal pressure, reduced pressure or increased pressure. It is needless to say that the contact is carried out under conditions such as concentration, temperature and pressure, which allow the solution composition to maintain its solution state.

In the present invention, bis-β-hydroxyethyl terephthalate having a small content of ions, that is, 50 ppm or less of anions and/or cations as impurities based on the bis-β-hydroxyethyl terephthalate is obtained after the solution composition has been contacted with the ion exchangers.

According to the results of studies conducted by the present inventors, a polyester obtained by using the bis-β-hydroxyethyl terephthalate obtained by the second process of the present invention as at least one of its raw materials can be used for various molded products such as fibers, films and bottles without causing a problem.

As described above, when a solution composition containing bis-β-hydroxyethyl terephthalate obtained by depolymerizing a recovered or waste polyester with ethylene glycol or by carring out the first process of the present invention is an intended object in the present invention, there is such an advantage that the solution composition containing bis-β-hydroxyethyl terephthalate having a small content of ions obtained by carrying out the second process of the present invention can be recycled as a raw material for the production of polyethylene terephthalate directly or after bis-β-hydroxyethyl terephthalate having a small content of ions is separated from the solution. In this case, bis-β-hydroxyethyl terephthalate having a small content of ions and more excellent whiteness can be obtained by carrying out a decoloring step, for example, treating with activated carbon at least one of the solution composition before the second process of the present invention is carried out, while the second process of the present invention is carried out, for example, during contact with a cation exchanger and an anion exchanger, and the intended product obtained after the second process of the present invention is carried out.

Bis-β-hydroxyethyl terephthalate having a total ion content of 50 ppm or less in the solute, obtained by the second process of the present invention, surprisingly differs from conventionally known bis-β-hydroxyethyl terephthalate having a total ion content of more than 50 ppm in behavior when they are placed under the same conditions. For example, when a solution composition containing crude bis-β-hydroxyethyl terephthalate containing 2,080 ppm of cations and 22 ppm of anions without a cation and anion removing step was concentrated until the content of a substance having a boiling point lower than that of bis-β-hydroxyethyl terephthalate became 5.0 wt % and subjected to molecular distillation, the obtained bis-β-hydroxyethyl terephthalate was colored to such an extent that it could be apparently recognized visually, the formation rate of an oligomer during molecular distillation was as high as 9.2%, for example, and the precipitate sticked to and accumulated on the heat transfer surface of a still, thereby impeding stable heat transfer at the time of distillation and reducing the recovery of bis-β-hydroxyethyl terephthalate to 69.2%, for example. On the other hand, when a solution composition containing crude bis-β-hydroxyethyl terephthalate which has been subjected to a cation and anion removing step by the second process of the present invention to reduce the content of cations to 10 ppm and the content of anions to 0 ppm was concentrated under the same conditions and subjected to molecular distillation under the same conditions, the obtained bis-β-hydroxyethyl terephthalate was not colored, the formation rate of an oligomer during molecular distillation was 0.7%, for example, the precipitate did not stick to the heat transfer surface of the still, thereby making possible stable continuous operation, and the recovery of bis-β-hydroxyethyl terephthalate was 98.1%, for example. Thus, when bis-β-hydroxyethyl terephthalate having a small content of ions, obtained by the second process of the present invention, is subjected to molecular distillation, extremely high purity bis-β-hydroxyethyl terephthalate can be obtained. The expression "molecular distillation" as used herein does not denote boiling-point distillation at a distillation temperature and pressure, that is, equilibrium distillation, but non-equilibrium distillation that the molecules of once evaporated bis-β-hydroxyethyl terephthalate move unidirectionally from the evaporation surface to the condensation surface, without substantially returning to the evaporation surface again.

Bis-β-hydroxyethyl terephthalate obtained by carrying out the second process of the present invention can be used as at least one of raw materials for the re-production of a high-quality polyester, in the form of a solution as it is or in the form of a solution whose concentration has been adjusted to an appropriate level or upon being subjected to a recrystallization step or distillation step.

In the present invention, the contents of anions and cations in bis-β-hydroxyethyl terephthalate are obtained and defined as follows.

Cation Content:

Determined by an inductively coupled plasma atomic emission spectrometry (ICP-AES).

(1) Pretreatment

After a sample containing ethylene glycol and bis-β-hydroxyethyl terephthalate was heated to about 80° C. to prepare a uniform solution, about 11 g of the solution was weighed, transferred to a conical beaker and heated to about 220° C. to remove ethylene glycol. Then, 20 ml of sulfuric acid was added and heated, and nitric acid was added in an amount of 1 ml at a time until nitrogen oxide was not formed any longer so as to decompose an organic substance.

(2) Measurement

The resultant sample was cooled to room temperature, 5 ml of hydrochloric acid and ultra pure water were added to the sample to prepare 100 ml of a specimen solution, and the weight of cations contained in the specimen solution was measured by the ICS-AES. The cations to be measured were Na, Mg, Ca, Fe, Co, Zn, Ti, Sn, Sb, Ge and P, and the total weight of these was taken as the cation content.

(3) Measuring Instruments

A moisture content is measured with a Karl Fischer moisture meter of Kyoto Denshi Kogyo KK. ICS-AES is carried out with the model ICAP-575 of Nippon Jarel Ash Co., Ltd.

Anion Content:

Determined by an ion chromatography.

(1) Pretreatment

A sample containing ethylene glycol and bis-β-hydroxyethyl terephthalate was heated to about 80° C. to prepare a uniform solution. Then, about 11 g of the solution was weighed and 100 ml of ultra pure water was added to this solution. The resulting solution was shaken to extract an ion component into a water phase.

(2) Measurement

The extracted water phase was filtered with a 0.2 μm medium filter, and the weight of anions was measured by an ion chromatography. The anions to be measured were Cl, Br, F, $NO_2$, $NO_3$, $PO_4$ and $SO_4$, and the total weight of these anions was taken as the anion content.

(3) Measuring Instruments

The IC-7000S ion chromatograph manufactured by Yokogawa Electric Corporation was used.

The Ion Pac AS4A-SC metering column of Dionecs Co., Ltd. was used to measure $NO_2$, $NO_3$, $PO_4$, Cl and Br, and the Ion Pac AS12A metering column of Dionecs Co., Ltd. was used to measure F.

A detailed description will be subsequently given of the third process of the present invention.

It has been heretofore proposed to purify crude bis-β-hydroxyethyl terephthalate to a high level by recrystallization and not by evaporation and distillation. However, though bis-β-hydroxyethyl terephthalate obtained by this method is just as if it has high quality, impurities still remain practically and become obstacles to the acquisition of a high-quality polyester in most cases. Especially when a polyester is to be obtained again by recovering a polyester and depolymerizing it into bis-β-hydroxyethyl terephthalate with ethylene glycol, such obstacles are markedly observed in most cases. Meanwhile, it has been proposed to obtain purified bis-β-hydroxyethyl terephthalate by evaporation or distillation purification. In this case, when crude bis-β-hydroxyethyl terephthalate is subjected to evaporation or distillation operation, a condensation reaction which becomes an obstacle to the operation occurs markedly, thereby making it difficult to obtain a bis-β-hydroxyethyl terephthalate fraction for practical use.

According to the results of studies conducted by the present inventors, it has been found that the obstacles in the evaporation or distillation of bis-β-hydroxyethyl terephthalate can be eliminated by using bis-β-hydroxyethyl terephthalate and/or a low condensate thereof having an extremely small total content of cations and anions, which is obtained by the second process of the present invention, as described above.

In the third process of the present invention, a bis-β-hydroxyethyl terephthalate-containing mixture to be purified by distillation has a cation and anion total content of 50 ppm or less and an ethylene glycol content of more than 10 wt % and further contains a compound having a boiling point lower than that of bis-β-hydroxyethyl terephthalate. This bis-β-hydroxyethyl terephthalate-containing mixture can be prepared by carrying out the second process of the present invention. In the third process of the present invention, the measurement methods and definitions of cations, anions and the contents thereof are the same as those described for the second process.

The total ion content of the bis-β-hydroxyethyl terephthalate-containing mixture is preferably 40 ppm or less, more preferably 30 ppm or less. The smaller total ion content is more advantageous. However, to reduce the total ion content to 10 ppm or less, a more complicated deionizing step is required, which is uneconomical. When the lower limit of total ion content is about 30 ppm, evaporation or distillation can be carried out substantially smoothly. When economy is not taken into account, the most preferred total ion content is 10 ppm or less. The appropriate total anion content is 1 ppm or less.

To achieve the above-mentioned total ion content of cations and anions, ion exchangers, especially ion exchange resins, are preferably used. In this case, it is practical that a cation and/or anion removing treatment should be made on a composition containing bis-β-hydroxyethyl terephthalate, especially a solution containing ethylene glycol as a main solvent and bis-β-hydroxyethyl terephthalate as a main solute. The cation removing treatment and/or the anion removing treatment may be carried out sequentially in any order or simultaneously. Similar to the second process, the Amberlite cation exchange resins (of Rohm and Haas Japan Co., Ltd.) can be given as examples of the ion exchange resin suitable for the cation removing treatment and the Amberlite anion exchange resins (of Rohm and Haas Japan Co., Ltd.) can be given as examples of the ion exchange resin suitable for the anion removing treatment. A method known per se can be used to carry out the step using these ion exchange resins, but when cation and/or anion removing operation is to be carried out, a temperature condition and the concentration of bis-β-hydroxyethyl terephthalate in a solution containing ethylene glycol as a main solvent and bis-β-hydroxyethyl terephthalate as a main solute are suitable selected to ensure that bis-β-hydroxyethyl terephthalate does not precipitate in the solution and the ion exchange resins can be used stably.

That is, it is advantageous that in carrying out an ion exchange resin treatment, a crude bis-β-hydroxyethyl terephthalate-containing mixture should contain more than 10 wt %, preferably more than 30 wt % of ethylene glycol. The above content of ethylene glycol is desired to maintain a solution state without precipitating bis-β-hydroxyethyl terephthalate in the deionization treatment, achieve a deionizing effect and carry out deionizing operation stably.

Further, before or after the above deionization treatment, preferably before the deionization treatment, a decoloring treatment is preferably carried out. It is advantageous that the decoloring treatment is an adsorbent treatment such as an activated carbon treatment.

The crude bis-β-hydroxyethyl terephthalate-containing mixture obtained by the deionization treatment still contains ethylene glycol in the above range, but its cation and anion total content has been reduced to 50 ppm or less.

In the third process of the present invention, this mixture is first subjected to preliminary evaporation or distillation to distill off a compound having a boiling point lower than that of bis-β-hydroxyethyl terephthalate.

The temperature and pressure at this point are selected to ensure that ethylene glycol and the compound having a boiling point lower than that of bis-β-hydroxyethyl terephthalate contained in the above mixture are distilled off. Stated specifically, the temperature is 170° C. or lower, preferably 100 to 150° C. and the pressure (absolute pressure) is 40,000 Pa (300 mmHg) or less, preferably 20,000 Pa (150 mmHg), more preferably 130 Pa (1 mmHg) to 13,300 Pa (100 mmHg).

This preliminary evaporation or distillation is carried out to reduce the content of ethylene glycol in the mixture to 10 wt % or less, preferably 5 wt % or less, particularly preferably 2 wt % or less. By reducing the content of ethylene glycol to the above range, the low-boiling compound excluding ethylene glycol is sufficiently removed and moreover, the distillation residue (may be referred to as "crude bis-β-hydroxyethyl terephthalate" in a sense that it is further purified in the following step) which has been concentrated to such an extent that the subsequent evaporation or distillation step can be advantageously carried out is obtained.

The step of distilling off the compound having a lower boiling point than that of bis-β-hydroxyethyl terephthalate by the preliminary evaporation or distillation under reduced pressure has such an advantage that at least one of the comonomer components of a polyester is removed. Examples of this third component include some of those will be given as examples of various components hereinafter. Out of these, isophthalic acid and 1,4-cyclohexane dimethanol are substantially removed, which is markedly advantageous.

In the third process of the present invention, the residue obtained by the preliminary evaporation or distillation as described above is further evaporated or distilled under reduced pressure to obtain purified bis-β-hydroxyethyl terephthalate. The crude bis-β-hydroxyethyl terephthalate which is the above evaporation or distillation residue preferably has a cation and/or anion total content of 50 ppm or less, preferably 40 ppm or less, more preferably 30 ppm or less.

When the above mixture having a cation and anion total content of 50 ppm or less is directly evaporated or distilled under reduced pressure without the above preliminary evaporation or distillation, it is difficult to carry out the evaporation or distillation operation under reduced pressure efficiently, and it is not advantageous from the viewpoint of obtaining an intended high-quality product.

The temperature of evaporation or distillation under reduced pressure is preferably in the range of 130 to 250° C., more preferably 160 to 220° C. The pressure (absolute pressure) is preferably 300 Pa (2.25 mmHg) or less, more preferably 70 Pa (0.5 mmHg) or less.

The average residence time of bis-β-hydroxyethyl terephthalate in an evaporator or still is 2 hours or less, preferably 1.5 hours or less.

The purified bis-β-hydroxyethyl terephthalate obtained by the purification of evaporation or distillation under reduced pressure has extremely high quality and a cation and anion total content of 15 ppm or less, preferably 5 ppm or less. Further, the purified bis-β-hydroxyethyl terephthalate has a bis-β-hydroxyethyl terephthalate content of 97 wt % or more, preferably 98 wt % or more.

The thus obtained purified bis-β-hydroxyethyl terephthalate is used in the production of polyethylene terephthalate or a copolyester thereof.

The purified bis-β-hydroxyethyl terephthalate obtained by the third process of the present invention is advantageously used as at least one of the raw materials of a polyester which is widely used for various purposes as described above. Stated specifically, the purified bis-β-hydroxyethyl terephthalate can be directly polymerized in the presence of a polymerization catalyst or polymerized together with terephthalic acid in the presence of a polymerization catalyst.

Any known polymerization catalysts may be used, as exemplified by antimony compounds, titanium compounds and germanium compounds.

Such polyester comprises ethylene terephthalate as a main constituent unit and encompasses a polyester containing a small amount of at least one other constituent component as a comonomer component. The permissible content of the comonomer component is generally 40 mol % or less, preferably 30 mol % or less, more preferably 20 mol % based on the total of all constituent units. Examples of the component to be copolymerized include, as the dicarboxylic acid component, aromatic dicarboxylic acids such as isophthalic acid, diphenyldicarboxylic acid, diphenylsulfonedicarboxylic acid, diphenylether dicarboxylic acid, naphthalenedicarboxylic acid, diphenoxyethanedicarboxylic acid and sodium sulfoisophthalic acid; aliphatic dicarboxylic acids such as sebacic acid and adipic acid; and alicyclic dicarboxylic acids such as hexahydroterephthalic acid, and, as the diol component, trimethylene glycol, tetramethylene glycol, hexamethylene glycol, cyclohexane dimethanol, bis-β-hydroxyethyl bisphenol A, bis-β-hydroxyethoxy diphenylsulfone, bis-β-hydroxyethoxydiphenyl ether, diethylene glycol, polyethylene glycol, and the like. Hydroxycarboxylic acids such as p-hydroxyethoxyphenylcarboxylic acid may be also used. Further, a polyfunctional compound having 3 or more functional groups and/or a monofunctional compound may be used in limits that the linearity of a polyester is maintained. Illustrative examples of the polyfunctional compound having 3 or more functional groups include trimesic acid, glycerin, pentaerythritol and the like, and illustrative examples of the monofunctional compound include diphenylmonocarboxylic acid, diphenylether monocarboxylic acid, phenoxypolyethylene glycol and the like. These comonomers may be used alone or in combination of two or more, as a functional derivative such as an ester.

According to the results of studies conducted by the present inventors, a polyester obtained by using the purified bis-β-hydroxyethyl terephthalate obtained by the third process of the present invention as at least one of its raw materials can be used in various molded products such as fibers, films and bottles extremely advantageously.

The fourth process of the present invention can be understood from a description of the evaporation or distillation under reduced pressure in the third process of the present invention.

Thus, according to the present invention, there is advantageously provided highly purified bis-β-hydroxyethyl terephthalate having a cation and anion total content of 15 ppm or less by the third process or the fourth process. This purified bis-β-hydroxyethyl terephthalate preferably has a cation and anion total content of 5 ppm or less. The purified bis-β-hydroxyethyl terephthalate preferably has a bis-β-hydroxyethyl terephthalate content of 97 wt % or more.

The above purified bis-β-hydroxyethyl terephthalate of the present invention can be advantageously used for the production of polyethylene terephthalate. That is, polyethylene terephthalate can be produced by polymerizing the above purified bis-β-hydroxyethyl terephthalate of the present invention in the presence of a polycondensation catalyst or by polymerizing the purified bis-β-hydroxyethyl terephthalate of the present invention and terephthalic acid in the presence of a polycondensation catalyst.

EXAMPLE

The following examples are provided for the purpose of further illustrating the present invention but are in no way to be taken as limiting.

Example 1

7 kilograms of pulverized flakes of a used PET bottle, 3 kg of polyethylene terephthalate short fibers containing no titanium as a delustering agent and 10 kg of bis-β-hydroxyethyl terephthalate were charged into a 240-liter autoclave equipped with a stirrer, and heated and stirred at 220° C. and normal pressure for one hour to pre-decompose the PET bottle and the polyethylene terephthalate short fibers so as to obtain a polyethylene terephthalate oligomer. To 20 kg of the obtained oligomer was added 40 kg of ethylene glycol and 0.07 kg of sodium methylate as a known ester exchange catalyst and the resulting mixture was heated and stirred at 200° C. and normal pressure for 2 hours to carry out depolymerization. An undecomposed product of polyethylene terephthalate was not observed visually in the solution obtained by depolymerization, and the depolymerized solution was transparent. Thereafter, 85 kg of normal-temperature ethylene glycol was added to this depolymerized solution and the temperature was further lowered to 55° C. to obtain a solution containing ethylene glycol as a main solvent and bis-β-hydroxyethyl terephthalate as a main solute. The whole solution was subjected to a decoloring treatment with activated carbon at a temperature of 55° C.

and then to a cation removing treatment with a cation exchange resin (Amberlite IR120-B of Rohm and Haas Japan Co., Ltd.) and an anion removing treatment with an anion exchange resin (Amberlite IRA-400 of Rohm and Haas Japan Co., Ltd.). This deionized solution was charged into a 500-liter autoclave equipped with a stirrer and vacuum pump to distill off ethylene glycol at a temperature of 135° C. under a pressure of 10,670 Pa (80 mmHg) until the weight of the residual ethylene glycol contained in the solution became 20% and then, concentrated with a vacuum thin film evaporator having a heat transfer area of 0.5 m² at a temperature of 150° C. under a pressure of 200 Pa (1.5 mmHg) until the content of the compound having a boiling point lower than that of bis-β-hydroxyethyl terephthalate became 5.0 wt %, to obtain a composition containing crude bis-β-hydroxyethyl terephthalate. Further, the composition containing crude bis-β-hydroxyethyl terephthalate was subjected to molecular distillation with a molecular still having a heat transfer area of 0.5 m² at a temperature of 200° C. and a pressure of 24 Pa (0.18 mmHg) for 75 minutes to obtain purified bis-β-hydroxyethyl terephthalate. The analytical values of quality of the obtained purified bis-β-hydroxyethyl terephthalate are shown in Table 1.

TABLE 1

| | |
|---|---|
| 1. optical density | 0.059 |
| 2. acid value (KOH mg/g) | 0.4 |
| 3. saponification number (KOH mg/g) | 439 |
| 4. melting point (° C.) | 112 |
| 5. whiteness | L = 98.7, a = −0.7, b = 1.2 |
| 6. total weight of cations (ppm) | 0.76 |
| 7. total weight of anions (ppm) | 0 |
| 8. bis-β-hydroxyethyl terephthalate (wt %) | 97.93 |
| 9. mono-β-hydroxyethyl terephthalate (wt %) | 1.33 |
| 10. oligomer (wt %) | 0.74 |

The term "optical density" as used in Table 1 denotes an index for evaluating the quality of bis-β-hydroxyethyl terephthalate and is an amount proportional to the content of a colored substance. This was obtained by measuring the absorbance of a 10% methanol solution of bis-β-hydroxyethyl terephthalate at a wavelength of 380 μm and a cell length of 10 mm. The whiteness was measured with a color difference meter and expressed by L (lightness), a (redness) and b (yellowness) values according to a Hunter method.

500 Grams of normal-temperature powders of the obtained purified bis-β-hydroxyethyl terephthalate was placed in a 1,000 cc glass polymerizer equipped with a stirrer the inside of which was fully substituted with nitrogen gas and heated to 130° C. under a nitrogen gas atmosphere to melt bis-β-hydroxyethyl terephthalate. 2.7 Grams of a solution containing 0.2 part of weight of hexagonal germanium dioxide completely dissolved in ethylene glycol which has reached its boiling point was added as a polymerization catalyst under a nitrogen gas atmosphere, the temperature was elevated to the boiling point (197° C.) of ethylene glycol under stirring for 20 minutes, and heating and stirring were further carried out at 197° C. and normal pressure for 45 minutes to obtain a polyethylene terephthalate oligomer. Subsequently, the oligomer was polycondensed at 280° C. and 90 Pa (0.7 mmHg) for 2 hours to obtain polyethylene terephthalate. The analytical values of quality of the obtained polyethylene terephthalate are shown in Table 2. The purified bis-β-hydroxyethyl terephthalate and polyethylene terephthalate were both extremely excellent quality for practical use.

TABLE 2

| | |
|---|---|
| 1. intrinsic viscosity ([η]) | 0.695 |
| 2. diethylene glycol (wt %) | 1.11 |
| 3. carboxyl terminal group (μeq/g) | 9.9 |
| 4. whiteness | L = 83.0, a = −2.2, b = −4.5 |

The intrinsic viscosity in Table 2 was measured in orthochlorophenol at 30° C. The whiteness was measured with a color different meter and expressed by L (lightness), a (redness) and b (yellowness) values according to a Hunter method.

Comparative Example 1

7 kilograms of pulverized flakes of a used PET bottle, 3 kg of polyethylene terephthalate short fibers containing no titanium as a delustering agent and 72 kg of ethylene glycol were charged into a 240-liter autoclave equipped with a stirrer, 0.07 kg of sodium methylate was added as a known ester exchange catalyst, and the resulting mixture was heated and stirred at 200° C. and normal pressure to depolymerize the PET bottle and polyethylene terephthalate short fibers. An undecomposed product of the polyethylene terephthalate was existent in the solution obtained by depolymerization, and the depolymerized solution was semi-opaque. This whole depolymerized solution was cooled to 55° C. and at this temperature subjected to a decoloring treatment with activated carbon and then to a cation removing treatment with a cation exchange resin (Amberlite IR120-B of Rohm and Haas Japan Co., Ltd.) and an anion removing treatment with an anion exchange resin (Amberlite of Rohm and Haas Japan Co., Ltd.). However, the undecomposed product of polyethylene terephthalate was instantly blocked in the ion exchange resin, thereby making impossible stable operation.

Example 2

(1) 53 Kilograms of crushed flakes of a used PET bottle (made from a polyethylene terephthalate resin) and 298 kg of ethylene glycol were charged into a 1,000-liter autoclave equipped with a stirrer, 0.27 kg of sodium methylate was added as a known ester exchange catalyst to depolymerize the PET bottle at 200° C. and normal pressure for 4 hours, and the whole obtained solution containing ethylene glycol as a main solvent and bis-β-hydroxyethyl terephthalate as a main solute was subjected to a decoloring treatment with activated carbon by reducing the temperature of this solution to 55° C. to obtain 350 kg of a crude solution. The total weight of cations contained in this concentrated solute of the crude solution was 2,080 ppm and the total weight of anions was 22 ppm. 150 Kilograms of this crude solution was subjected to a cation removing treatment with a cation exchange resin (Amberlite IR120-B of Rohm and Haas Japan Co., Ltd.,) at a temperature of 55° C. and to an anion removing treatment with an anion exchange resin (Amberlite IRA-400 of Rohm and Haas Japan Co., Ltd.). The total weight of cations contained in the concentrated solute of the deionized solution was 9.4 ppm and the total weight of anions was 0 ppm.

(2) This deionized solution was charged into a 500-liter autoclave equipped with a stirrer and vacuum pump to distill off ethylene glycol at 135° C. and 10,670 Pa (80 mmHg) until the weight of the residual ethylene glycol in the solution became 20 wt %. Thereafter, the solution was concentrated by a vacuum thin film still having a heat transfer area of 0.5 m² at 150° C. and 200 Pa (1.5 mmHg) until the content of a substance having a boiling point lower than that of bis-β-hydroxyethyl terephthalate became 5.0 wt % to obtain 31.6 kg of a composition containing bis-β-hydroxyethyl terephthalate. 31.6 Kilograms of this composition containing bis-β-hydroxyethyl terephthalate was subjected to molecular distillation with a molecular still having a heat transfer area of 0.5 m² at a temperature of 200° C. and a pressure of 24 Pa (0.18 mmHg) for 75 minutes to obtain 29.4 kg of purified bis-β-hydroxyethyl terephthalate. The operation results of Example 2 are shown in Table 3. The analytical values of quality of the obtained purified bis-β-hydroxyethyl terephthalate are shown in Table 4.

TABLE 3

| | |
|---|---|
| amount of solution treated with molecular still (kg) | 31.6 |
| treatment time of molecular still (minutes) | 74.5 |
| amount of purified bis-β-hydroxyethyl terephthalate recovered (kg) | 29.4 |
| recovery rate of purified bis-β-hydroxyethyl terephthalate (%) | 98.1 |
| amount of formed oligomer (kg) | 0.21 |
| formation rate of oligomer (%) | 0.7 |

TABLE 4

| | |
|---|---|
| optical density | 0.059 |
| acid value (KOH mg/g) | 0.4 |
| saponification number (KOH mg/g) | 439 |
| melting point (° C.) | 112 |
| whiteness | L = 98.7, a = −0.7, b = 1.2 |
| total weight of cations (ppm) | 0.76 |
| total weight of anions (ppm) | 0 |
| bis-β-hydroxyethyl terephthalate (wt %) | 97.93 |
| mono-β-hydroxyethyl terephthalate (wt %) | 1.33 |
| oligomer (wt %) | 0.74 |

The term "optical density" as used in Table 4 denotes an index for evaluating the quality of bis-β-hydroxyethyl terephthalate and is an amount proportional to the content of a colored substance. This was obtained by measuring the absorbance of a 10% methanol solution of the purified bis-β-hydroxyethyl terephthalate at a wavelength of 380 μm and a cell length of 10 mm. The whiteness was measured with a color difference meter and expressed by L (lightness), a (redness) and b (yellowness) values according to a Hunter method.

(3) 500 Grams of normal-temperature powders of the obtained purified bis-β-hydroxyethyl terephthalate was placed in a 1,000 cc glass polymerizer equipped with a stirrer the inside of which was fully substituted with nitrogen gas and heated to 130° C. under a nitrogen gas atmosphere to melt the bis-β-hydroxyethyl terephthalate. 27.2 Grams of a solution containing 0.2 wt % of hexagonal germanium dioxide completely dissolved in ethylene glycol which has reached its boiling point was added as a polymerization catalyst under a nitrogen gas atmosphere, the temperature was elevated to the boiling point (197° C.) of ethylene glycol under stirring for 20 minutes, and heating and stirring were further carried out at 197° C. and normal pressure for 45 minutes to obtain a polyethylene terephthalate oligomer. Subsequently, this oligomer was polycondensed at 280° C. and 90 Pa (0.7 mmHg) for 2 hours to obtain polyethylene terephthalate. The analytical values of quality of the obtained polyethylene terephthalate are shown in Table 5.

The purified bis-β-hydroxyethyl terephthalate and polyethylene terephthalate were both extremely excellent quality for practical use.

TABLE 5

| | |
|---|---|
| intrinsic viscosity ([η]) | 0.695 |
| diethylene glycol (wt %) | 1.11 |
| carboxyl terminal group (μeq/g) | 9.9 |
| whiteness | L = 83.0, a = −2.2, b = −4.5 |

The intrinsic viscosity in Table 5 was measured in orthochlorophenol at 30° C. The whiteness was measured with a color different meter and expressed by L (lightness), a (redness) and b (yellowness) values according to a Hunter method.

Example 3

The operation of Example 2 was repeated except that 100 kg of a crude solution which was subjected to a decoloring treatment in Example 2 was subjected to a cation removing treatment alone without an anion removing treatment. The results of this operation are shown in Table 6.

TABLE 6

| | |
|---|---|
| amount of solution treated with molecular still (kg) | 21 |
| treatment time of molecular still (minutes) | 49.7 |
| amount of purified bis-β-hydroxyethyl terephthalate recovered (kg) | 17.5 |
| recovery rate of purified bis-β-hydroxyethyl terephthalate (%) | 87.4 |
| amount of formed oligomer (kg) | 0.74 |
| formation rate of oligomer (%) | 3.7 |

The obtained bis-β-hydroxyethyl terephthalate was colored light yellow to an extent that it could be recognized visually, the formation rate of an oligomer during molecular distillation was 3.7% and there was hardly observed a phenomenon that the precipitate sticked to and accumulated on the heat transfer area of the still. The recovery of the bis-β-hydroxyethyl terephthalate at this point was 87.4%.

Comparative Example 2

The operation of Example 2 was repeated except that 100 kg of a crude solution which was subjected to a decoloring treatment in Example 2 was not subjected to cation and anion removing treatments. The results of this operation are shown in Table 7.

TABLE 7

| | |
|---|---|
| amount of solution treated with molecular still (kg) | 21 |
| treatment time of molecular still (minutes) | 49.7 |
| amount of purified bis-β-hydroxyethyl terephthalate recovered (kg) | 13.8 |
| recovery rate of purified bis-β-hydroxyethyl terephthalate (%) | 69.2 |
| amount of formed oligomer (kg) | 1.84 |
| formation rate of oligomer (%) | 9.2 |

The obtained bis-β-hydroxyethyl terephthalate was colored yellow brown which could be recognized visually, the formation rate of an oligomer during molecular distillation was high at 9.2%, stable continuous distillation operation was difficult because the precipitate sticked to and accumulated on the heat transfer area of the still, and the recovery rate of the bis-β-hydroxyethyl terephthalate was as low as 69.2%.

The invention claimed is:

1. A process for producing bis-β-hydroxyethyl terephthalate and/or a low condensate thereof from an aromatic polyester, comprising the steps of:
   heating the aromatic polyester comprising terephthalic acid as a main dicarboxylic acid component and ethylene glycol as a main glycol component together with bis-β-hydroxyethyl terephthalate and/or a low condensate thereof in an amount of 1 part by weight of the aromatic polyester and 0.1 to 4.5 parts by weight of the bis-β-hydroxyethyl terephthalate and/or the low condensate thereof in the absence of free ethylene glycol to decompose the aromatic polyester, and then,
   reacting the decomposed product with ethylene glycol in an amount of 1 part by weight of the decomposed product and 3.0 to 10.0 parts by weight of ethylene glycol to convert the terephthalic acid component of the decomposed product into bis-β-hydroxyethyl terephthalate and/or a low condensate thereof having a molar ratio of ethylene glycol to terephthalic acid between 10.6 and 40.5, wherein each of said low condensates is a compound containing ethylene terephthalate as the main constituent component and has an average polymerization degree of 1 to 10.

2. The process of claim 1, wherein the pre-decomposition is carried out by heating the bis-β-hydroxyethyl terephthalate and/or low condensate thereof to melt.

3. The process of claim 1, wherein the pre-decomposition is carried out at a temperature of 150 to 265° C.

4. The process of claim 1, wherein the pre-decomposition is carried out using 0.7 to 1.2 parts by weight of the bis-β-hydroxyethyl terephthalate and/or low condensate thereof based on 1 part by weight of the aromatic polyester.

5. The process of claim 1, wherein a reaction between the pre-decomposed product and ethylene glycol is carried out at a temperature of 190 to 265° C.

6. The process of claim 1, wherein the reaction between the pre-decomposed product and ethylene glycol is carried out using 1 part by weight of the pre-decomposed product and 3.0 to 5.0 parts by weight of ethylene glycol.

* * * * *